United States Patent [19]

Nelson et al.

[11] Patent Number: 5,797,130
[45] Date of Patent: Aug. 18, 1998

[54] METHOD FOR TESTING PROFICIENCY IN SCREENING IMAGES OF BIOLOGICAL SLIDES

[75] Inventors: Alan Caril Nelson, Redmond; Shih-Jong James Lee, Bellevue, both of Wash.

[73] Assignee: NeoPath, Inc., Redmond, Wash.

[21] Appl. No.: 526,138

[22] Filed: Sep. 5, 1995

Related U.S. Application Data

[63] Continuation of Ser. No. 153,293, Nov. 16, 1993, abandoned.

[51] Int. Cl.$^6$ .......................... G06F 159/00; G06F 17/60
[52] U.S. Cl. .......................... 705/11; 705/2; 364/551.01; 382/133; 382/224
[58] Field of Search ............... 705/2, 3, 11; 364/551.01; 382/133, 128, 224

[56] References Cited

U.S. PATENT DOCUMENTS

| | | | |
|---|---|---|---|
| 5,257,182 | 10/1993 | Luck et al. | 364/413.1 |
| 5,287,272 | 2/1994 | Rutenberg et al. | 364/413.01 |
| 5,301,685 | 4/1994 | Guirguis | 128/760 |

OTHER PUBLICATIONS

Newspaper article, source unknown, dated Oct. 20, 1991, titled: "Misread Pap test cost mother her life".

Tanaka, et al.: "Automated Cytologic Screening System for Uterine Cancer Utilizing Image Analysis Processing", published Oct. 22, 1981, pp. 279-285.

Watanabe, et al: "A Pap Smear PreeScreening System: Cybest", published 1978, pp. 227-240.

Koss, et al.: "Evaluation of the PAPNET™ Cytologic Screening System for Quality Control of Cervical Smears", published Feb. 1994; manuscript received Jan. 20, 1993.

Attachment to above (item T) entitled: "Clinical studies Using the PAPNET system".

Dialog file 635; Acc #0197940 91-19512: Gordon Lee, "Neo Path Inc.: Investors Attracted by Analysis Potented of Pap Smear System" Seattle Times, v. 114, n. 48, SD, p. 2, Feb. 25, 1991.

*Primary Examiner*—David R. Hudspeth
*Assistant Examiner*—Joseph Thomas
*Attorney, Agent, or Firm*—Hans I. Sun; Emil Moffa

[57] ABSTRACT

An automatic screening apparatus that screens all pap smear slides called normal by cytotechnologist. These normal pap smears will contain the mistakes, false negatives, which must be recovered as a measure of the cytotechnologist's performance. Additionally, these mistakes must be discovered to improve the quality of the laboratory services. The automated screening machine after rescreening the normals, rank orders of the pap smears with those "normals" most likely to be missed ranked at the top. Another human screener re-examines those pap smears with high ranking to determine if the first human screener misclassified the pap smear. Mistakes are recovered and the performance of the first screener is assessed. Proficiency testing is accomplished with 100% quality control.

7 Claims, 5 Drawing Sheets

METHOD FOR TESTING PROFICIENCY IN SCREENING IMAGES OF BIOLOGICAL SLIDES

This is a continuation of application Ser. No. 08/153,293,filed on Nov. 16, 1993 now abandoned.

This invention relates to a method and apparatus for testing the performance of human screeners who analyze images and, more particularly, to a system for testing the performance of cytotechnologists.

BACKGROUND OF THE INVENTION

Cytotechnologists screen pap smears for indications of abnormality. During screening, mistakes may occur at unacceptably high rates. These mistakes are called false negatives and are costly. The United States Government requires that cytotechnologists be proficiency tested to assess their screening accuracy. This requirement has been enacted as the Clinical Laboratory Improvement Amendment of 1988 ("CLIA Act of 1988"). The CLIA Act of 1988 specifies that 10% of all inspections be repeated as part of the quality control process and additionally that proficiency testing must be implemented.

Even though retesting of 10% of those slides already screened is known and required, the problem caused by false negatives has not been solved. The prior art has attempted to use examination of standard sets of pap smear slides in such testing but the results are believed to be biased since the cytotechnologist is aware of being tested. Also, the prior art does not provide any method of recovering mistakes of the cytotechnologist.

The objective of proficiency testing, therefore, is to provide an accurate and timely assessment of the screening performance of the cytotechnologist under normal working conditions. In other words, ultimately the performance of the cytotechnologists should be evaluated while screening slides.

Fundamentally, a testing system should be more accurate than the system being tested. Timely assessment is critical to facilitate positive change. Either the cytotechnologist must be unaware of being tested or know that testing occurs continuously under normal working conditions. Finally, the cost of testing must be justified by the resulting benefit.

In trying to achieve these goals, prior art methods used a standard slide set test where diagnostic truth is established by consensus. Unfortunately, there are practical problems involved with the standard slide set test including the problems of creating a test so that the cytotechnologist is unaware of the test when being tested, having enough slides per test set, and testing the cytotechnologist regularly. Finally, a consensus must be achieved concerning the classification of the standard slides.

Other prior art workers have proposed rescreening the cytotechnologist's workload of normal slides by a second trained screener with discrepancies being resolved by a third. The true result is determined to be the result which occurs in two out of three screenings. This approach is very expensive.

Practical concerns with rescreening spring from the fact that only a small percentage of the normal workload yields positives.

Another drawback in the prior art is that the 10% random rescreening proficiency test provided in the CLIA Act of 1988 is an ineffective test for measuring proficiency. For example, consider the hypothetical case where 5% of the patient population is abnormal and the cytotechnologist has a 10% false negative rate. The cytotechnologist screening at the CLIA limit will miss about 90 positives per year categorizing these falsely as negatives or "normals". In such a case, a 10% random sample of slides characterized as "normals" will recover only 8 to 9 positives. Such recovery rates indicate that 10% random rescreening may not be enough to provide a likelihood that true positive slides will be detected at an acceptable rate.

It is, therefore, the motive of the invention to provide a method and apparatus that not only increases the quality of proficiency testing, but also provides a method for analyzing the very slides that are false negatives in order to ensure a high degree of quality control.

SUMMARY OF THE INVENTION

The invention provides an automatic screening apparatus and method that screens all pap smear slides characterized as normal by the cytotechnologist. These "normal" pap smears will typically contain the true normals and mistakes, and false negatives which must be recovered as a measure of the cytotechnologist's performance. Additionally, these "normal" pap smears then must be re-examined to improve the quality control effort of the laboratory. The automated screening apparatus rank orders the pap smears with those pap smears classified as "normals" most likely to be abnormals having the highest ranking. Another human screener re-examines those pap smears with high ranking to determine if the first human screener misclassified the pap smear. Mistakes are recovered and the performance of the first screener is assessed.

In a further aspect of the invention, a method is provided for image analysis of images including other CRT and microscope images like pap smear images, naked eye inspections and radiographs such as used for mammograms and other diagnostic medical images.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

DETAILED DESCRIPTION OF THE PREFERRED EMBODIMENT

Figure 1:
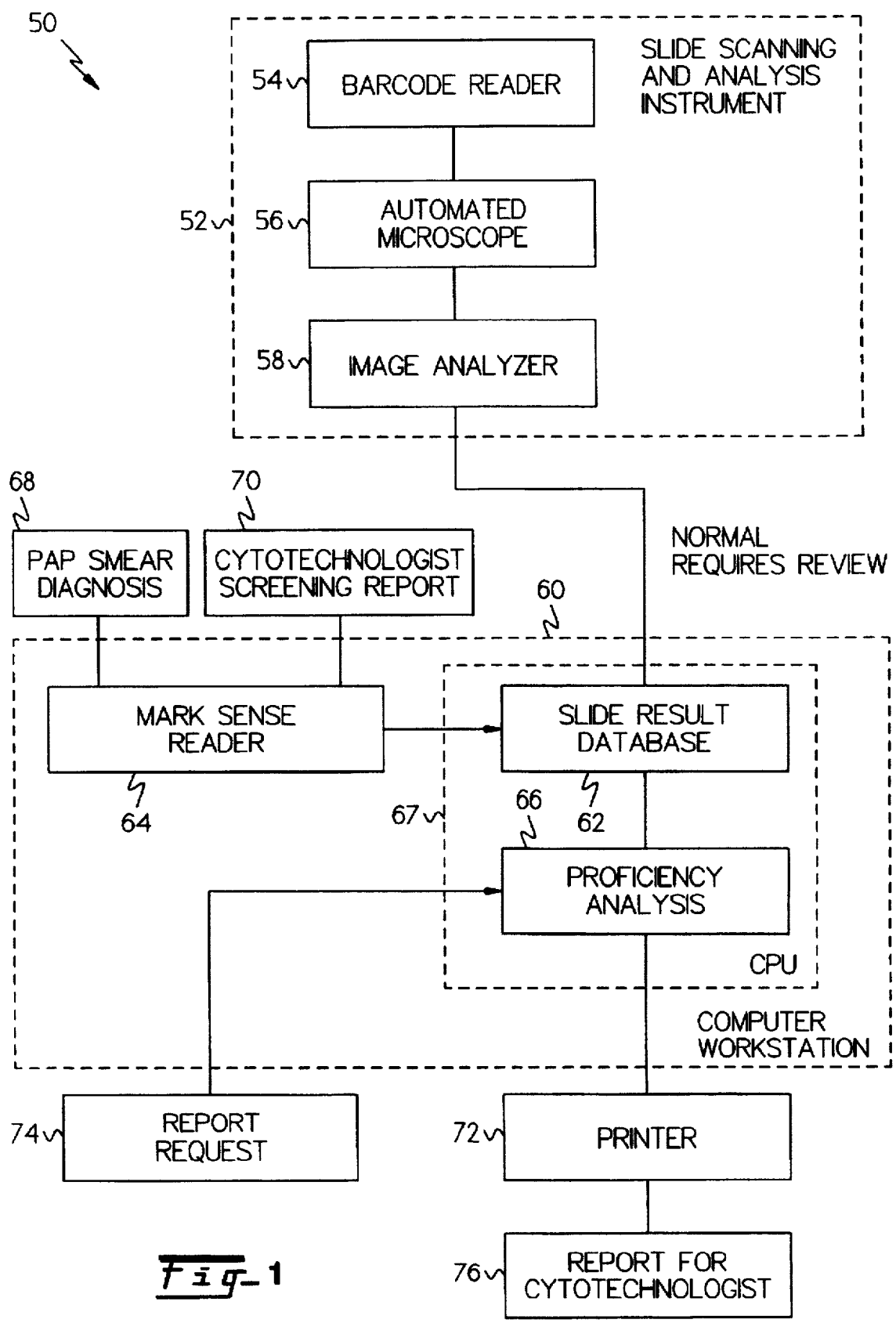
FIG. 1 shows a schematic block diagram of one embodiment of the invention for proficiency testing.

Referring now to FIG. 1, FIG. 1 shows a schematic block diagram of one embodiment of the apparatus of the invention used for proficiency testing. The proficiency testing apparatus 50 is comprised of a slide inspection and analysis instrument 52, a computer work station 60 and an optional printer 72. The slide inspection and analysis instrument 52 may advantageously be further comprised of a conventional bar code reader 54, a conventional automated microscope 56, and an image analyzer 58 constructed and arranged to operate as an automated pap smear screener. One example of such an automated pap smear screener is the "Autopap 300™" brand automated screener built by NeoPath, Inc. of Bellevue, Wash. The computer work station 60 may advantageously be further comprised of a computer processing unit 67 including a proficiency analysis engine 66, a slide result database 62, and a conventional mark sense reader 64. The printer 72 may be coupled to the computer work station 60 to print a cytotechnologist's report 76 in response to an external report request 74, for example.

In operation, the proficiency testing apparatus of the invention 50 is used by a cytotechnologist to aid in the quality control and proficiency testing of biological slides. In one specific embodiment of the apparatus of the invention, the slides are pap smear slides. In one preferred embodiment, the bar code reader 54 is controlled and used by an automated microscope to scan in the bar code of the slide in question. The automated microscope then examines the slide and an image analyzer 58 determines whether the slide is a normal slide or an abnormal slide. The image analyzer also ranks the slides on a relative scale of those slides most likely to be abnormal. The image analyzer communicates to the computer work station 60 where the results of the slide inspection are stored in a slide result database 62.

Additionally, a cytotechnologist screening report 70 may be read into the slide result database 62 by mark sense reader 64. Pap smear diagnosis information 68, including actual disease information, may also be input through the mark sense reader 64.

Figure 2:
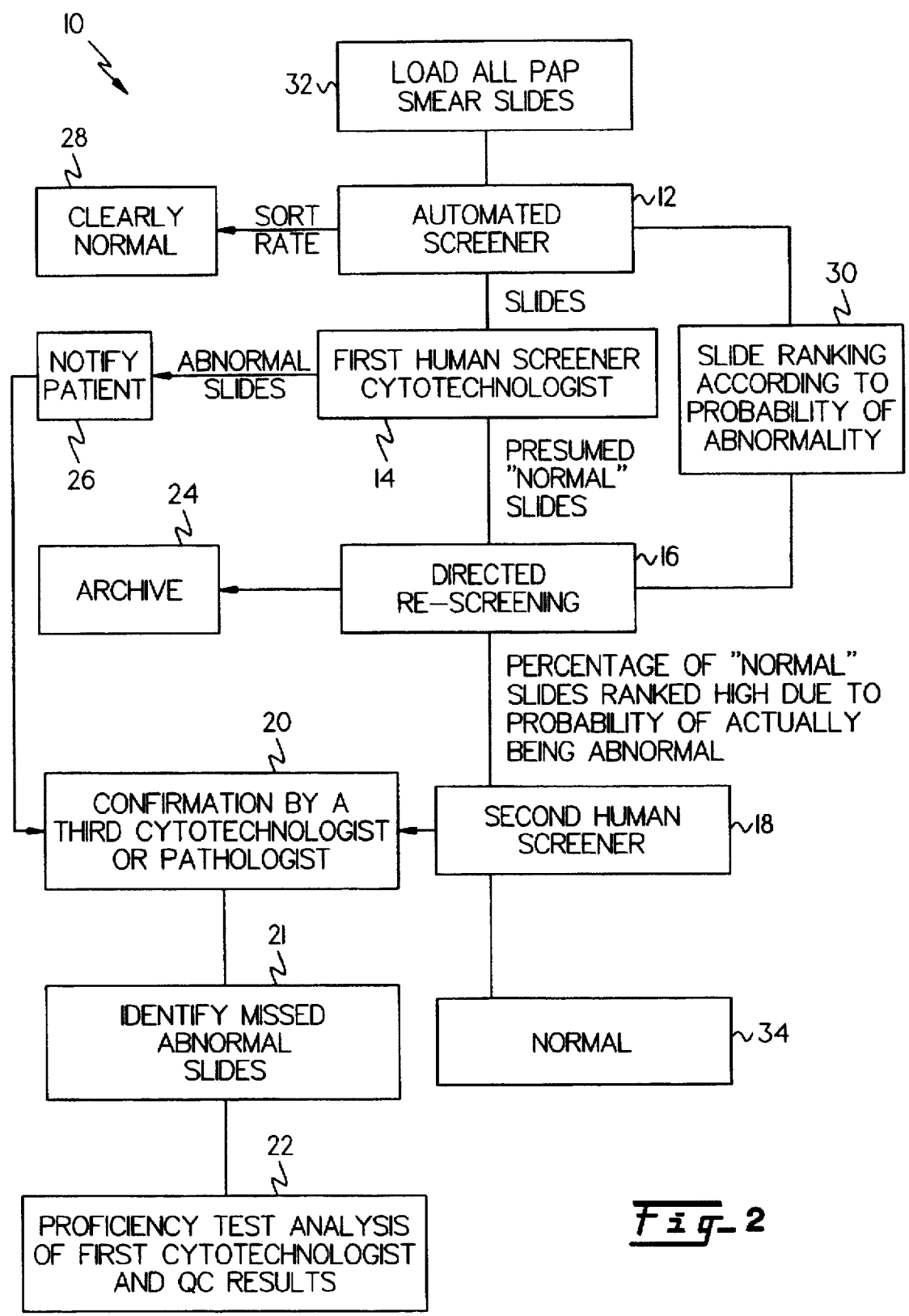
FIG. 2 shows a flow diagram of the method of the invention used to increase reliability of a proficiency test wherein a machine is used to perform initial screenings on slides.

Referring now to FIG. 2, FIG. 2 shows a method of the invention used to increase the reliability of a screening proficiency test and for providing quality control inspection. At step 32, the process loads all samples, in one embodiment pap smear slides, into the "Autopap 300™" brand automated screener. The process flows to step 12 where the automated screener inspects all the samples. A certain number of the samples are clearly normal. The "Autopap 300™" brand automated screener can discern these clearly normal samples. A preset threshold is set as a percentage of the total number of slides. This is known as the sort rate. Sort rate is the percentage of clearly normal slides called normal compared to the total population of normal slides. The sort rate may be, in one embodiment, set at 20%. These slides are classified as clearly normal in step 28. The slides that are not classified as clearly normal are sent to a first human screener, typically a cytotechnologist, in step 14.

The "Autopap 300™" brand automated screener process also provides a slide ranking of all slides according to the probability of abnormality in step 30. The ranking process selects some percentage of high ranked slides as a directed re-screening population. The percentage may be, in one preferred embodiment, set at 20%. Those skilled in the art will recognize that there are many ways to assign such probabilities based on features found in pap smear specimens.

At step 14, the first human screener screens out normal slides in accordance with known practice. The slides classified as normal at this stage are sent to a process step known as directed rescreening, step 16. The first human screener may also determine that some slides are abnormal. The slides determined to be abnormal are sent to process 26 where the patient is notified of the abnormality. The directed rescreening slides, typically about 20% of the presumed normal population, are selected for rescreening in step 16. The selected slides are re-screened in step 18 by a second human screener, typically a cytotechnologist applying known techniques.

The directed rescreening process 16 is done in one specific embodiment on a computer work station which is interfaced to the "Autopap 300™" brand automated screener as shown in FIG. 1. The second human screen process 18 may determine that some of the slides are normal according to a predetermined criteria. In one embodiment, 80% of the slides may be judged normal and not require rescreening. These slides are archived in step 24 as directed rescreening.

The predetermined percentage of the normal slides that ranked high in step 16 most likely are abnormal or have a high probability of being abnormal and are rescreened by the second human screener in step 18. The slides that the second human screener determines as being abnormal are confirmed by a third cytotechnologist or pathologist in step 20. Missed abnormal slides are identified at step 21. The second human screener may also determine that certain slides are normal. These slides are sent to step 34 for normal processing. The confirmed abnormal slides are sent through a proficiency test analysis program step 20 running on the work stations shown in FIG. 1. Proficiency test analysis is performed for each cytotechnologist. The quality control results are accumulated according to the methods of FIG. 4 and FIG. 5.

In one embodiment of the invention, the sort rate may be set at 0. In this case all slides are sent to step 14 for the first human screener and none are classified as clearly normal at step 28. To save costs and screening time in an alternative embodiment of the invention, the sort rate may be set at a nominal 20%.

Now referring to Table A, Table A shows that of 2000 test slides, the "Autopap 300™" brand automated screener automatically screened out 20% of the work load as normal correctly. In other words, of the four lab tests, with sort rates set at 19, 25, 22 and 33, respectively, a 0 false negative rate was achieved each time.

TABLE A

| "Autopap 300 ™" Automatically Screens out 20% of Workload as Normal | | |
|---|---|---|
| 2000 Slides | Sort Rate (X) | False Negative Rate (FNR) - High Grade |
| Lab 1 | 19 | 0 |
| Lab 2 | 25 | 0 |
| Lab 3 | 22 | 0 |
| Lab 4 | 33 | 0 |

In one embodiment of the invention, the second human screener may receive a directed rescreening at the rate of 20%, of the highest ranking slides where the slides are ranked according to probability of abnormality.

Those skilled in the art will appreciate that other medical image analysis may be the subject of inspection. These other images include other CRT and microscope images like pap smear images, naked eye inspections and radiographs such as used for mammograms and other diagnostic medical images.

Now referring to Table B, Table B shows test results indicating that the method of the invention recovers approximately eight-fold more missed positives than the 10% quality control method of the prior art. In the test, 2000 slides were run through four laboratory experiments by NeoPath, Inc. The slides contained low grade squamous interepethlial lesions and high grade squamous interepethlial lesions and cancerous cells. The directed rescreening was set at 20% for the simulated run. In each case, the method of the invention recovered between 69% and 96% of the missed positives versus the 10% quality control method of the prior art which identified 10% of the missed positives on average.

TABLE B

"Autopap 300 ™" Automatically Recovers 8-Fold More Missed Positives Than 10% Quality Control
(Units: Sensitivity %)

| 2000 Slides | LSIL | HSIL | Cancer |
|---|---|---|---|
| Lab 1 | 69 | 82 | NA |
| Lab 2 | 70 | 81 | 88 |
| Lab 3 | 75 | 81 | NA |
| Lab 4 | 81 | 95 | 96 |

It can be seen that the proficiency testing of the invention provides continuous testing of the cytotechnologist. As a result, laboratory performance and quality control methods are improved significantly. The cost is relatively the same as prior methods with only a small additional burden for the case of a 0% sort rate, and with substantially no additional burden for the case of a 20% sort rate.

In one example of the invention's effectiveness, the cytotechnologist screening at the CLIA limit may miss about 90 positives per year whereas the method of the invention may recover at least 70 of those missed positives.

By combining quality control with continuous testing for proficiency, a cytotechnologist may likely be unaware of being tested at all times as part of their normal work flow. Thus, the result is less biased and, in addition, more mistakes may be recovered.

Figure 3:
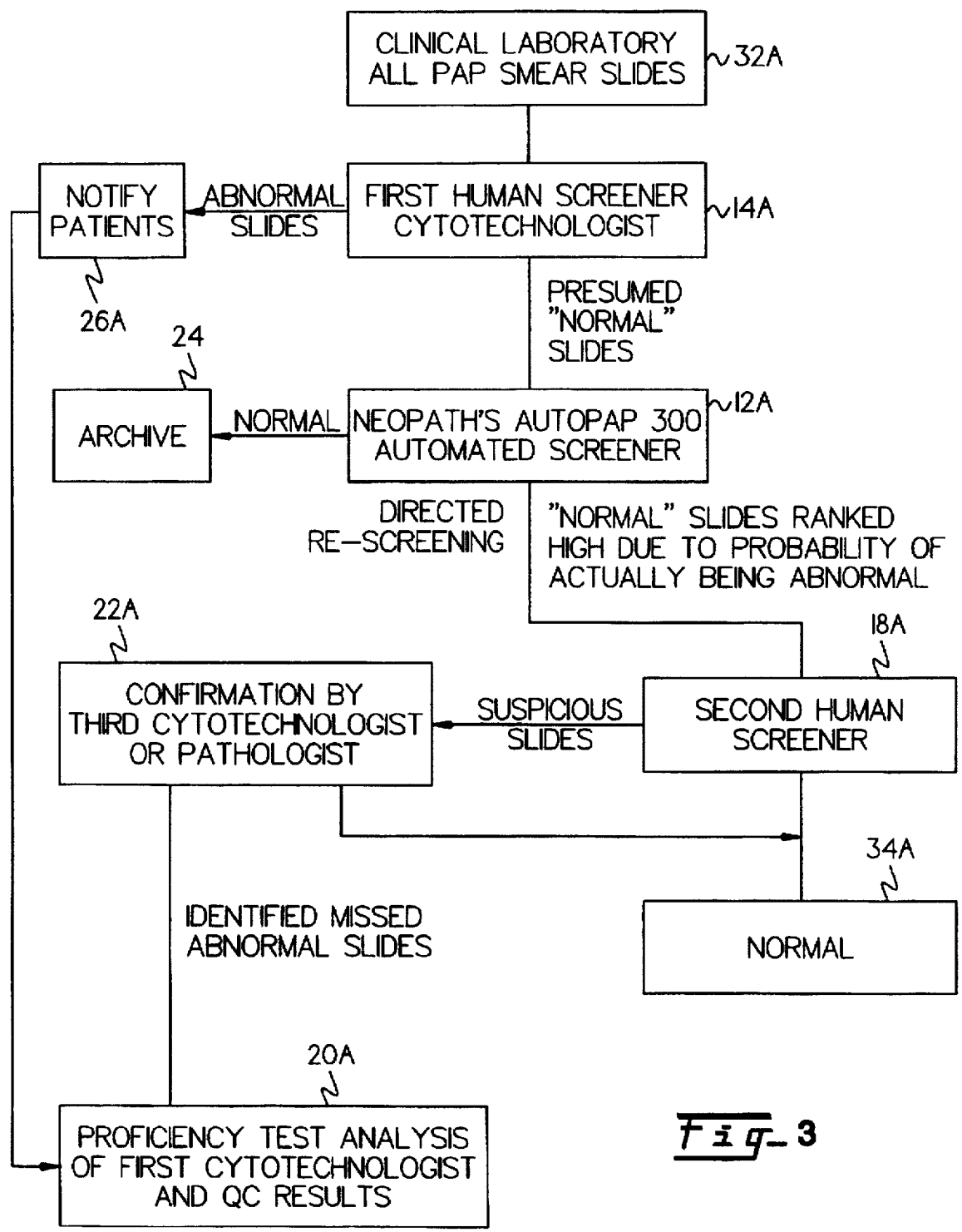
FIG. 3 shows a schematic flow diagram of the method of the invention wherein a human screener is used to perform initial screening on slides.

Now referring to FIG. 3. FIG. 3 shows a schematic flow chart for a more specific method of the invention wherein a human screener screens the slides first. The process starts at step 32A where pap smear slides are prepared in a known way. The process then flows to step 14A wherein a first human screener cytotechnologist determines whether slides are abnormal or normal. Any slides determined to be abnormal are sent to step 26A where the patients are notified. The process flows to step 12A where any presumed normal slides are loaded into an automated screener. The automated screener then determines that a certain number of slides are clearly normal and these are archived in step 24. The slides that are not clearly normal are sent for a directed rescreening in step 18A. The automated screener ranks normal slides based on the probability of actually being abnormal. The second human screener in step 18A determines suspicious slides by applying known techniques. These are confirmed by a third cytotechnologist or pathologist in step 22A. Identified missed abnormal slides are logged into the work station in step 20A. The work station performs a proficiency test analysis of the first cytotechnologist and compiles quality control results. One example of a proficiency test analysis is described hereinbelow in detail. Slides that are determined to be normal are archived in step 34A.

Figure 4:
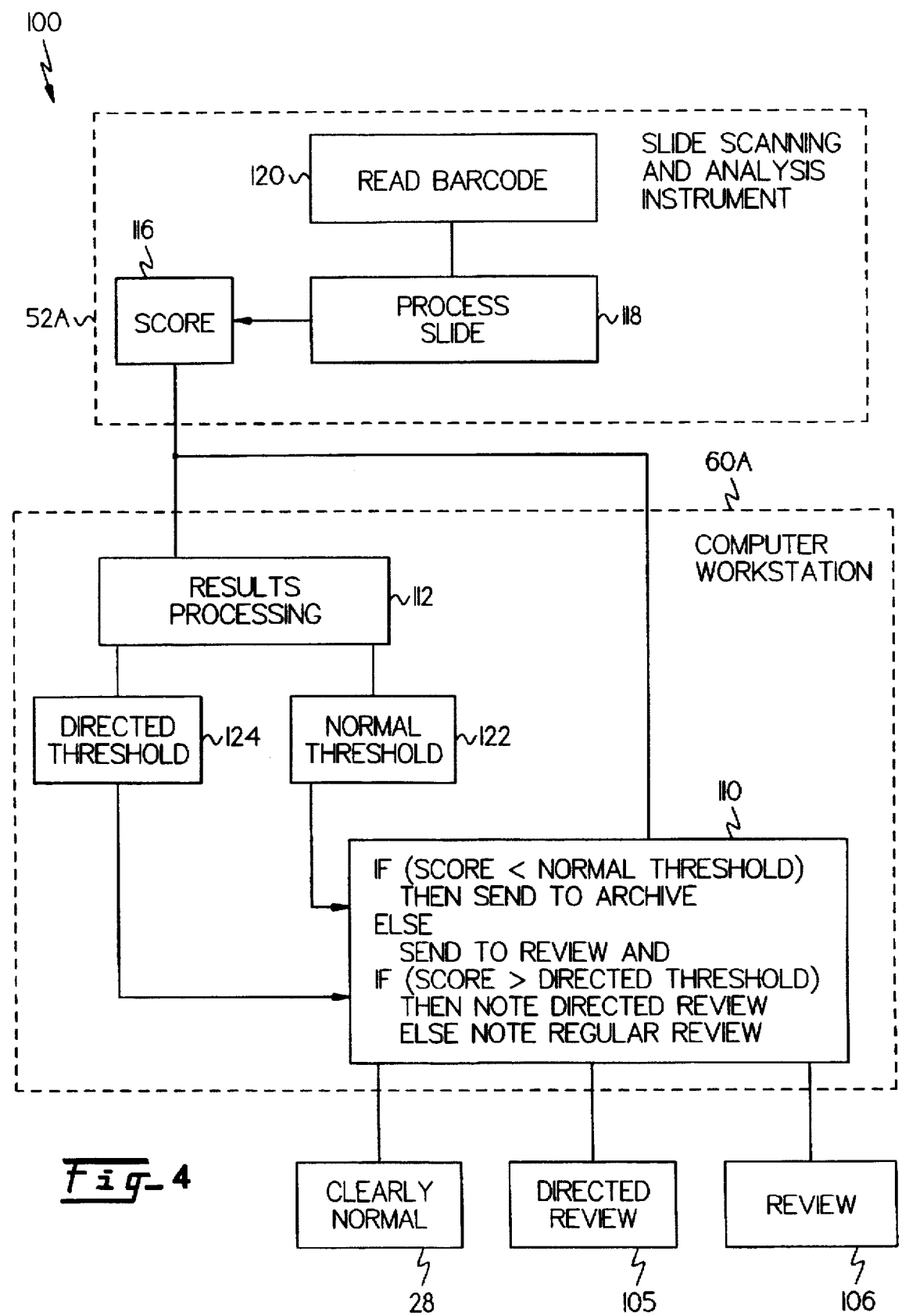
FIG. 4 shows a schematic flow chart of a processing sequence employed in one method of the invention using a machine-first procedure.

Now referring to FIG. 4. FIG. 4 shows a processing sequence for a machine-first procedure of the method of the invention. The procedure starts with reading a bar code on a slide in step 120. The bar code reading in step 120, the processing of the slide in step 118 and scoring 116 is done by the slide scanning analysis instrument 52A in one preferred embodiment of the invention. An automated slide screener may be used for this purpose. The bar code on each slide is read in step 120 and then each slide is processed in step 118 to determine whether it is a normal or abnormal slide. The process flows to step 116 to score the slide. The score is sent to a results processor at step 112. The results processor accumulates the scores of all processed slides and determines two thresholds, a directed threshold 124 and a normal threshold 122 by rankings of the scores. The normal threshold may be set in order to yield the desired sort rate of slides identified as clearly normal. This depends upon the number of normal slides and the distribution of scores. The directed threshold is set in a similar manner, depending upon the percentage desired for directed review and the distribution of scores. The score is also sent to step 110 to apply the decision logic. If the slide is determined to be normal, it is archived. If it is not, then if the review score is greater than a directed threshold, then the directed review is noted 105 or else a regular review 106 is noted. The slides are then sent to be archived in step 28 or for review in step 106 or for directed review as the case may be.

One specific example of an inspection results processing for machine-first analysis may be done according to the following steps:

(1) Slide scores are entered into results database.

(2) Scores for slides are ranked and directed review threshold and normal review thresholds are determined.

(3) Slides with scores less than the normal review threshold are sent to the slides archive.

(4) Slides with scores greater than or equal to the normal review threshold are sent to review and those slides with scores greater than the directed review threshold are noted for their higher probability for abnormalities.

Figure 5:
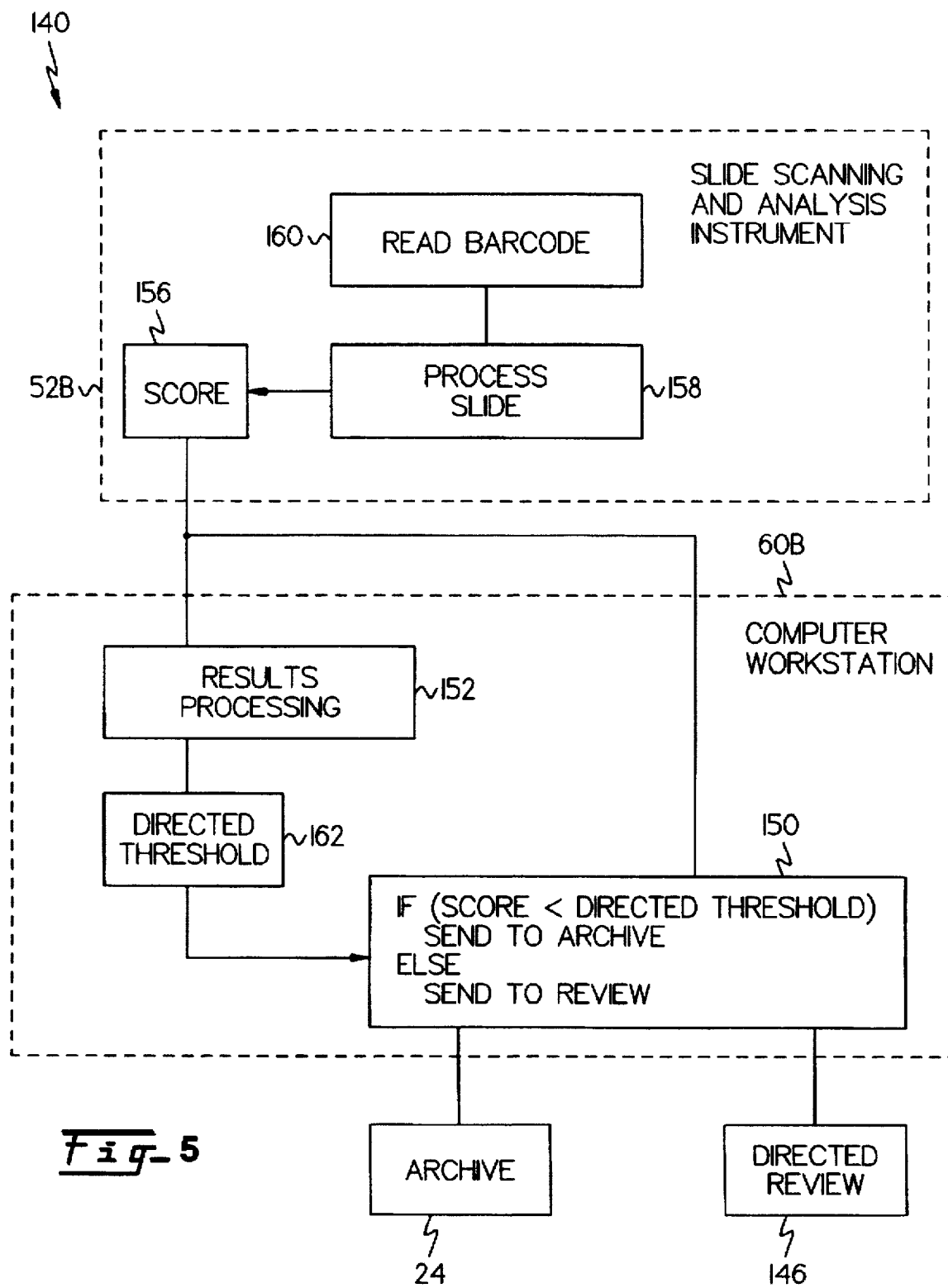
FIG. 5 shows a schematic flow chart of a processing sequence employed in one method of the invention using a human-first procedure.

Referring now to FIG. 5. FIG. 5 shows the process sequence for a human screener procedure of FIG. 3. The slide scanning analysis instrument 52B performs the bar code reading at step 160 and the slide processing at step 158. The computer work station performs the results processing at steps 150 and 152. Once again, the score, as determined at step 156, is sent to both processes at step 150 and 152. In step 150 if the score is less than the directed threshold indicated at step 162, the slide is archived at step 24 or else it is sent for directed review in step 146. Step 152 accumulates the scores of processed slides and determines a directed threshold by ranking of the scores. Thresholds may be adjusted depending upon the types of slides being reviewed.

One specific example of a method for inspection results processing for human-first analysis may be done according to the following steps:

(1) Slide scores are entered into results database.

(2) Scores for slides are ranked and directed review threshold is determined.

(3) Slides with scores less than the directed review threshold are sorted as normal and those with scores greater than or equal to the directed review threshold are sent to review.

Having described the apparatus and major steps of the invention in detail processes used for proficiency test analysis and inspection results processing are described below.

A proficiency test analysis procedure may be done according to the following steps:

(1) Input the name of the cytotechnologist to be tested (C1).

(2) Input a time period T for the test. For example, T=6 months.

(3) Input an abnormal diagnosis type for test (D). The diagnosis type examples may include low grade SIL (Squamous Interepethlial Lesion), high grade SIL, squamous carcinoma, etc.

(4) Input the pass-fail threshold value ($V_T$) for the proficiency test score.

(5) Acquire from a database the total number of abnormal slides of the selected type D detected by C1: Nd, in the period T, where Nd is the number detected.

(6) Acquire from a database the total number of abnormal slides of the selected type D missed by C1: Nm, in the period T, where Nm is the number missed.

(7) The proficiency test score (PTS) is generated based on the following rule:

$$PTS = N\_d/(N\_d + N\_m + 1)$$

the score ranges are [0,1]. That is, 0<=PTS<1.

(8) The proficiency test result decision logic is

| IF (PTS >= T) | THEN PASS |
|---|---|
| ELSE | FAIL |

In one preferred embodiment of the invention, the test is implemented according to FIG. 1.

One specific example of proficiency analysis may be done according to the following steps:

(1) Slide scores are entered into results database 62.

(2) Slide accession numbers and laboratory pap smear diagnoses are marked on mark sense forms. These forms are read in to the slide results database through the mark sense reader 64.

(3) Cytotechnologist screening results including cytotechnologist name, date and time of screening, slide accession numbers, and pap smear diagnoses are marked on mark sense forms. These forms are read into the slide results database by the mark sense reader 64.

(4) Report results for given cytotechnologist, time span and diagnosis type input to the proficiency analysis.

(5) Screening results for specified cytotechnologist detailing cytotechnologist screening results and laboratory pap smear diagnosis are derived from the results database.

(6) Reports for the cytotechnologist with name, time span, diagnosis type, proficiency test score, and proficiency test result are printed.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of machine aided continuous proficiency testing of human readers for biological slides, wherein the machine aided continuous proficiency testing occurs under nornal working conditions of a first human reader and is based on substantially all biological slides inspected by the first human reader, comprising the steps of:

(a) loading a plurality of biological slides into an automated slide inspection screening device;

(b) screening out obviously normal slides with the automated slide inspection screening device to obtain first result slides comprising slides not screened out as obviously normal;

(c) inspecting the first result slides by the first human reader and designating presumed normal slides;

(d) obtaining a rank ordering of probability of abnormality of the presumed normal slides from the automated slide inspection screening device;

(e) inspecting by a second human reader a predetermined percentage of the presumed normal slides most likely to be abnormal based on the rank ordering; and (f) proficiency testing the first human reader based on the presumed normal slides and compiling proficiency test results.

2. The method of claim 1 wherein after the step of inspecting by a second human reader, a third reader confirms the proficiency test results.

3. The method of claim 1 wherein the plurality of biological slides are acquired from a laboratory's routine slide population.

4. A method of integrating human and automated device screening for a continuous proficiency test of human readers of clinical pap smear slide inspection, wherein the continuous proficiency test is performed under normal working conditions of a first human reader and is based on substantially all biological slides inspected by the first human reader and designated as presumed normal slides, comprising the steps of:

(a) inspecting a plurality of slides for normality or abnormality and designating presumed normal slides by the first human reader;

(b) rescanning the presumed normal slides with an automatic screener and designating possible abnormal slides according to predetermined criteria;

(c) rescreening the possible abnormal slides by a second human reader and designating abnormal slides;

(d) confirming any abnormal slides by a third reader and designating confirmed abnormal slides; and (e) performing a proficiency test of the first human reader based on a proportion of presumed normal slides designated as confirmed abnormal slides by the third reader.

5. The method of claim 4 wherein the proficiency test further comprises the steps of:

(a) inputting a name of a first human reader to be tested;

(b) inputting a time period T for a test;

(c) inputting an abnormal diagnosis type for the test;

(d) inputting a pass-fail threshold value $\underline{V}_T$ for a proficiency test score;

(e) acquiring from a database a total number of abnormal slides of a selected type D detected by the first human reader: Nd, in the time period T;

(f) acquiring from the database the total number of abnormal slides of the selected type D missed by the first human reader: Nm, in the time period T; and (g) generating the proficiency test score based on the following rule:

$$PTS = N\_d/(N\_d + N\_m + 1).$$

6. The method of claim 5 wherein the abnormal diagnosis type comprises a type selected from the group consisting of low grade SIL (Squamous Interepithelial Lesion), high grade SIL, and squamous carcinoma.

7. The method of claim 5 wherein the proficiency test result decision logic comprises

| IF (PTS ≥ $V_T$) | THEN PASS |
|---|---|
| ELSE | FAIL. |

* * * * *